United States Patent [19]

Marinacci et al.

[11] Patent Number: 5,868,721
[45] Date of Patent: Feb. 9, 1999

[54] INJECTION DEVICE HAVING ANTI-CORING NEEDLE

[75] Inventors: Robert A. Marinacci, West Chester, Pa.; William Robert Pearson, Laurel, Md.; David Edward Spady, Centreville; N. Lawrence Dalling, Cross Junction, both of Va.

[73] Assignee: Meridian Medical Technologies, Columbia, Md.

[21] Appl. No.: 850,220

[22] Filed: May 1, 1997

Related U.S. Application Data

[62] Division of Ser. No. 545,148, Oct. 19, 1995, Pat. No. 5,716,348.

[51] Int. Cl.$^6$ ..................................................... A61M 5/32
[52] U.S. Cl. ........................... 604/272; 604/239; 604/413
[58] Field of Search ............................. 604/87, 117, 232, 604/234, 239, 244, 272–274, 411, 413

[56] References Cited

U.S. PATENT DOCUMENTS

| | | |
|---|---|---|
| 2,634,726 | 4/1953 | Hanson . |
| 2,748,769 | 6/1956 | Huber . |
| 4,413,993 | 11/1983 | Guttman . |
| 4,537,593 | 8/1985 | Alchas . |
| 4,889,529 | 12/1989 | Haindl . |
| 5,102,393 | 4/1992 | Sarnoff et al. . |
| 5,391,151 | 2/1995 | Wilmot . |

FOREIGN PATENT DOCUMENTS

WO 96/39213  12/1996  WIPO .

*Primary Examiner*—Ronald Stright, Jr.
*Assistant Examiner*—A. T. Nguyen
*Attorney, Agent, or Firm*—Cushman Darby & Cushman IP Group of Pillsbury Madison & Sutro LLP

[57] ABSTRACT

An injection device which includes a container constructed and arranged to contain a medicament, a medicament disposed within the container, a seal constructed and arranged to seal the medicament in the container, and a hypodermic needle. The hypodermic needle has a tubular, elongated, generally cylindrical wall defining an internal longitudinal bore extending longitudinally through the cylindrical wall along a longitudinal axis. The cylindrical wall forms a forward end defining a forward opening of the bore and a rearward end defining a rearward opening of the bore, the cylindrical wall having a laterally facing opening spaced closer to the rearward opening of the longitudinal bore than the forward opening of the longitudinal bore. The longitudinal bore is restricted at a position between the rearward opening and the laterally facing opening. The forward end has a point constructed and arranged to pierce an individual's flesh, the rearward end having a point constructed and arranged to pierce the seal so that the rearward opening and the laterally facing opening establish fluid communication with the medicament to enable the medicament to be dispensed through the bore and into the individual's flesh.

2 Claims, 2 Drawing Sheets

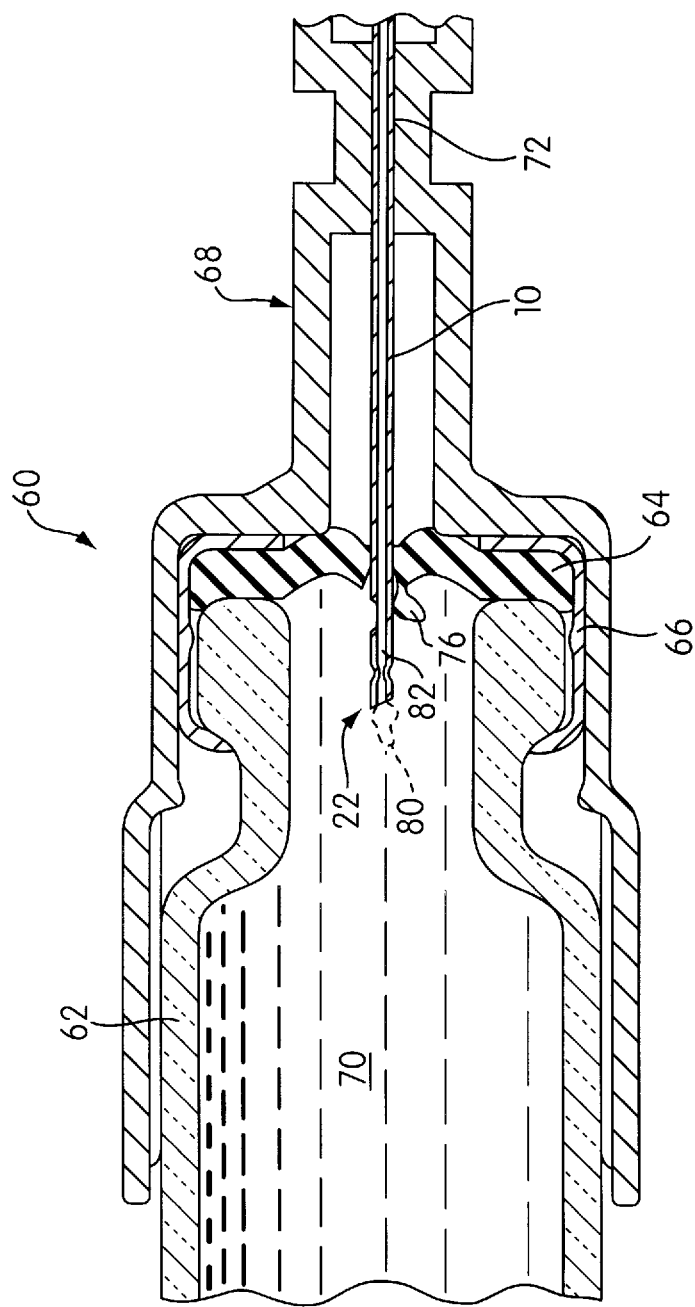

INJECTION DEVICE HAVING ANTI-CORING NEEDLE

This is a division of application Ser. No. 08/545,148, filed Oct. 19, 1995, now U.S. Pat. No. 5,716,348.

The present invention relates to hypodermic needles, and more particularly, to the type of hypodermic needles that have a rearward end adapted to establish fluid communication with a medicament prior to an injection operation.

Hypodermic needles have several applications. In most such applications the hypodermic needle has a forward end adapted to penetrate the skin of an individual, and a rearward end adapted to communicate with a liquid medicament source so that the medicament is permitted to travel from the source, through a central longitudinal bore in the needle, and into the flesh of the individual.

In many of the applications for hypodermic needles, it is necessary for the rearward end of the needle to puncture a seal in order to establish fluid communication with the medicament source. For example, one application exists in the field of automatic injection devices, wherein a liquid medicament is sealed within a tubular container, preferably made of glass, having a synthetic rubber seal closing off a forward end thereof. During an injection operation, the rearward end of the needle punctures the seal to establish fluid communication with the medicament, and a stressed spring assembly is released so as to cause the forward end of the needle to project outwardly from the forward end of automatic injector body and into the flesh of an individual while such fluid communication is maintained. A plunger rearwardly confines the medicament within the container and is driven by the released spring assembly towards the forward end of the container and functions to force the medicament through the needle and into the flesh of the individual. Such automatic injection devices are disclosed, for example, in U.S. Pat. Nos. 5,391,151; 5,102,393; and copending U.S. patent application Ser. No. 08/545,149, filed Oct. 19, 1995, now U.S. Pat. No. 5,716,348 which are hereby incorporated by reference.

A problem associated with the aforementioned arrangements in which the rearward end of the needle must puncture a rubber or other type of seal in order to establish fluid communication with a medicament is that it is possible for the rearward end of the needle to core out or dislodge a small particle from the seal. This can lead to problems associated with the needle establishing fluid communication with the medicament. For example, where a synthetic rubber seal is used, a synthetic rubber particle may become lodged in the needle's rearward end and significantly reduce the amount of medicament flow through the needle. While certain types of "anti-coring" rubber materials, such as natural rubber, have been used, such materials are not compatible with as many types of medicaments in comparison with synthetic rubber.

To obviate the aforementioned problems, there has been proposed a hypodermic needle in which a second, lateral opening is provided in the cylindrical side wall of the needle, towards the rearward end of the needle. The purpose of providing a second opening is to enable fluid to flow freely through the needle even in the event that the rearward opening is plugged with a rubber particle. However, this configuration does not address the potential for a relatively small rubber particle from entering the rearward end of the needle and becoming lodged within the bore of the needle at, or downstream from, the lateral second opening, thus impeding fluid flow through the needle. It also does not address another problem which may arise when a lateral second opening is provided. More specifically, rather than a particle becoming completely dislodged from the rubber seal, in some instances the particle may become tethered to the seal at the point of puncture. In such instances, it is possible for the tethered particle to be drawn partially into the second, lateral opening so as to partially block the longitudinal passage through the needle and thereby reduce flow through the needle. It may also be possible for a dislodged particle to partially enter the second, lateral opening and thereby reduce flow through the needle.

It is an object of the present invention to provide a hypodermic needle that overcomes the problems noted above. In accordance with the present invention, there is provided a hypodermic needle comprising a tubular, elongated, generally cylindrical wall defining an internal longitudinal bore extending longitudinally through the cylindrical wall along a longitudinal axis. The longitudinal bore has forward and rearward openings. The cylindrical wall is constructed and arranged to form a forward pointed end and a rearward pointed end. The rearward pointed end terminates in an annular end surface having a rearwardmost point lying in an imaginary plane disposed perpendicularly to the longitudinal axis. The annular rearward end surface defines an imaginary plane inclined with respect to the imaginary plane perpendicular to the longitudinal axis. The cylindrical wall has a laterally facing opening spaced from the rearward opening of the longitudinal bore, and the longitudinal bore is restricted at a position between the rearward opening and the laterally facing opening.

It is a further object to provide an injection device which incorporates an anti-coring needle. In accordance with this object, the present invention provides an injection device which includes a container constructed and arranged to contain a medicament, a medicament disposed within the container; a seal constructed and arranged to seal the medicament in the container, and a hypodermic needle. The hypodermic needle has a tubular, elongated, generally cylindrical wall defining an internal longitudinal bore extending longitudinally through the cylindrical wall along a longitudinal axis. The cylindrical wall forms a forward end defining a forward opening of the bore and a rearward end defining a rearward opening of the bore, the cylindrical wall having a laterally facing opening spaced closer to the rearward opening of the longitudinal bore than the forward opening of the longitudinal bore. The longitudinal bore is restricted at a position between the rearward opening and the laterally facing opening. The forward end has a point constructed and arranged to pierce an individual's flesh, the rearward end having a point constructed and arranged to pierce the seal so that the rearward opening and the laterally facing opening establish fluid communication with the medicament to enable the medicament to be dispensed through the bore and into the individual's flesh.

These and other objects, features, and advantages of the present invention will become apparent from the following description and the appended claims, taken in conjunction with the accompanying drawings.

BRIEF DESCRIPTION OF THE DRAWINGS

FIG. 6 is a longitudinal sectional view showing the hypodermic needle in accordance with the present invention, being utilized in conjunction with a dental cartridge assembly of an automatic injector assembly in accordance with the principles of the present invention.

DETAILED DESCRIPTION OF THE DRAWINGS

Figure 1:
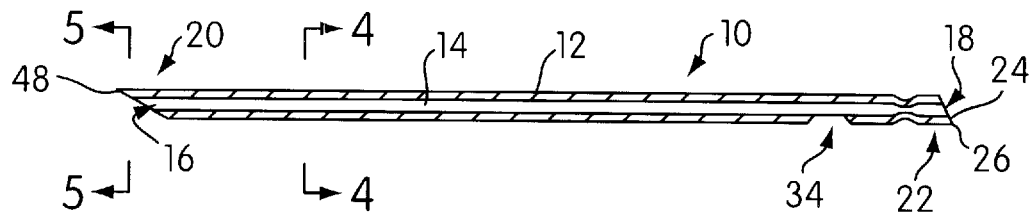
FIG. 1 is a longitudinal sectional view of the hypodermic needle according to the principles of the present invention.

Referring now, more particularly, to the drawings, there is shown in FIG. 1 a hypodermic needle, generally indicated at 10, in accordance with the principles of the present invention. The hypodermic needle comprises a tubular, elongated, generally cylindrical wall 12 defining an internal longitudinal bore 14 extending longitudinally therethrough along a longitudinal axis (indicated at x in FIG. 2). The longitudinal bore 14 has a forward opening 16 and a rearward opening 18. Preferably, the cylindrical wall 12 is made from type 304 stainless steel. The cylindrical wall has a forward pointed end, generally indicated at 20 formed by an angular grind. The cylindrical wall also has a rearward pointed end, generally indicated at 22, also formed by an angular grind. The rearward pointed end 22 is defined by and terminates in an annular end surface 24. As shown more clearly in FIG. 2, the rearward pointed end 22 terminates in a rearwardmost point 26 lying in an imaginary plane, indicated at 28, disposed perpendicularly to the longitudinal axis x. The annular rearward end surface 24 defines an imaginary plane, indicated at 32, inclined with respect to the imaginary plane 28 perpendicular to the longitudinal axis x.

The cylindrical wall 12 has a laterally facing opening 34 spaced from the rearward opening 18 of the longitudinal bore 14. As can be appreciated from the figures, the lateral opening 34 is in longitudinal alignment with the rearwardmost point 26. The cylindrical wall 12 is crimped or otherwise extended inwardly into the longitudinal bore 14 to form a restriction 38, which restricts the longitudinal bore 14 at a position between the rearward opening 18 and the laterally facing opening 34.

Figure 3:
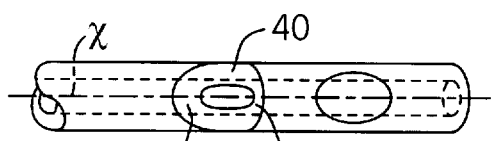
FIG. 3 is a plan view of the rearward portion of the hypodermic needle of the present invention, rotated 90° about the longitudinal axis with respect to FIG. 2.

As shown in FIG. 3, the lateral opening 34 is defined by an oblong surface, generally indicated at 40, defining a beveled edge surrounding the opening 34. The surface 40 defining the beveled edge converges as it approaches the longitudinal axis of the hypodermic needle.

Figure 2:
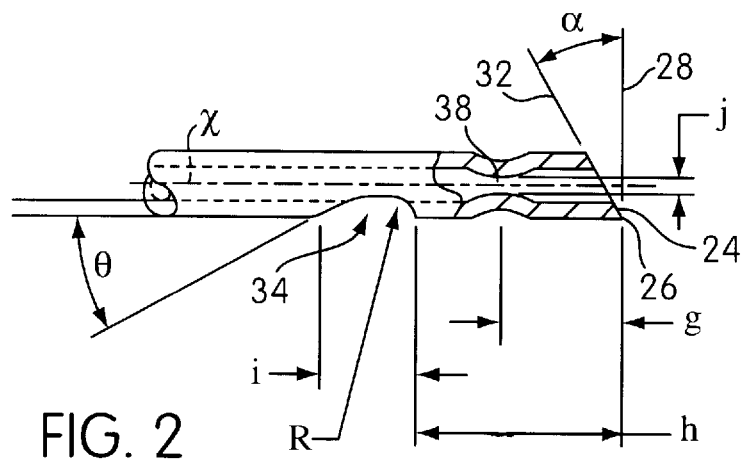
FIG. 2 is an enlarged longitudinal sectional view of the rearward portion of the hypodermic needle in accordance with the principles of the present invention.

From FIGS. 2 and 3, it can be appreciated that the more forwardly disposed portion 42 of surface 40 is inclined at a smaller angle with respect to the longitudinal axis x in comparison with the rearward portion 44 of surface 40. While the forwardly disposed surface portion 42 is substantially flat and forms an angle θ, preferably in the range of about 28°±1° with respect to the longitudinal axis, the rearward portion 44 is substantially arcuate so as to define an imaginary circle having a maximum radius R of 0.0060 inches.

The imaginary plane 32 defined by the annular end surface 24 forms an angle α with respect to the imaginary plane 28. Angle α is preferably about 30°±1°. The rearwardmost point 26 is disposed at a distance h from the center of the restriction 38. Preferably, the distance g is approximately 0.030 inches. The rearwardmost point 26 is disposed at a distance h from the closest edge forming the lateral opening 34. Preferably, the distance h is approximately 0.052 ±0.002 inches. The longitudinally rearwardmost and longitudinally forwardmost portions of the surface 40 forming the lateral opening 34 are spaced by a distance i. Preferably, the distance i is approximately 0.024 ±0.003 inches. The crimped or inwardly extending surfaces forming the restriction 38 are separated by a distance j. Preferably, the distance j is approximately 0.005 +0.001 to −0.002 inches. The thickness of the cylindrical wall is designated by reference character t. Preferably the thickness t is about 0.0050 +0.0010 to −0.0015 inches.

Figure 4:
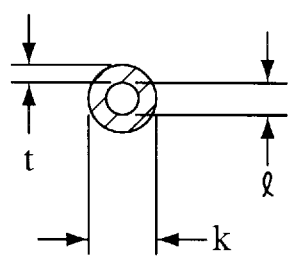
FIG. 4 is a transverse sectional view taken through the line 4—4 in FIG. 1.

Referring to FIG. 4, which is a sectional view taken through the line 4—4 in FIG. 1, it can be appreciated that the outer diameter for the major portion of the cylindrical wall 12 is a dimension k, which is preferably about 0.016–0.0165 inches (27 gauge). As can also be appreciated from FIG. 4, the cylindrical wall 12 has an inner diameter 1, which is preferably between about 0.0075 and 0.0090 inches.

Figure 5:
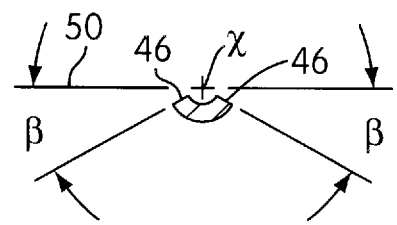
FIG. 5 is a transverse sectional view taken through the line 5—5 in FIG. 1.

Referring now to FIG. 5, which is a sectional view taken through the line 5—5 in FIG. 1, it can be appreciated that surfaces 46 forming the side surfaces leading to the forwardmost point 48 of the hypodermic needle are inclined by an angle β with respect to an imaginary plane 50 through axis x, as shown. In FIG. 1, it can be seen that the forwardmost point 48 is disposed on the opposite side of the needle (i.e., out of longitudinal alignment) with respect to rearwardmost point 26.

FIG. 6 is a longitudinal sectional view of the hypodermic needle of the present invention shown in cooperation with a dental cartridge assembly of an automatic injector. The dental cartridge assembly, generally indicated at 60 includes a glass container 62, a forwardly disposed rubber sealing disc 64, a metallic clamp ring 66, and a needle hub assembly 68. The clamp ring 66 is crimped around the forward end of the glass container 62 so as to enable the rubber sealing disc 64 to form a forward seal for medicament 70 contained within the glass container 62. The needle hub assembly 68 is fixed to the needle 10 at a position 72 by an epoxy or any conventional fashion. During an injection operation, the needle hub assembly 68 is caused to ride rearwardly with respect to the glass container 62 into the position shown in FIG. 6. During this movement of the needle hub assembly 68, the rearward pointed end 22 of the hypodermic needle 10 is caused to puncture the rubber sealing disk 64. The specifics of the injector device of this type can be more fully appreciated from co-pending U.S. patent application Ser. No. 08/280,884, hereby incorporated by reference, and the aforementioned incorporated U.S. Pat. Ser. No. 5,102,393 and U.S. patent application Ser. No. 08/545,149, filed on Oct. 19, 1995, now U.S. Pat Ser. No. 5,716,348

As shown in FIG. 6, the puncturing force of the hypodermic needle 10 has created a tethered rubber particle 76. Such tethered particle 76 will ordinarily be formed on a side of the needle opposite the rearwardmost point 26. The lateral opening 34 is preferably positioned generally on the same side of the needle as the rearwardmost point and most preferably the lateral opening 34 and rearwardmost point 26 are in longitudinal alignment with one another so that the tethered particle 76 will not interfere with the opening 34.

In many instances, the particle will be captured within the rearward opening 18 of the hypodermic needle, as generally indicated in the dashed line configuration 80, rather than being tethered as with tethered particle 76. Where the particle 80 becomes lodged in the rearward opening 18, the particle remains at such position, rather than being permitted to float within the medicament and perhaps find its way to the laterally facing opening 34, wherein it may block the bore 14 and severely restrict flow of medicament through the needle. The restriction 38 is provided in the cylindrical wall 12 in order to prevent any further forward travel of the particle through the bore 14 so that the particle does not become lodged within the bore at a more downstream position wherein it may completely prevent fluid flow. With the rearward opening 18 now substantially blocked by the particle, the medicament will flow into the bore 14 via the opening 34.

It should also be noted that the oblong shape of lateral opening 34 minimizes the likelihood of complete blockage thereof by a dislodged particle. In addition, the surface 40 and opening 34 are shaped so that they will not cause any further coring of the seal 64. More specifically, the arcuate rearward portion 44 (preferably defining an imaginary circle having a maximum radius of 0.0060 inches) is shaped such that the portion of the rubber seal 64 surrounding the puncture hole, and that slides along the exterior periphery of the cylindrical wall 12 as the rearward portion of the needle is moved through the seal 64, will be readily and smoothly accommodated. In addition, the gently sloping forward portion 42 (preferably forming an angle of about 28°±1° with respect to the longitudinal axis x) will gently expand the portions of seal 64 surrounding the puncture hole as such portions ride forwardly along the portion 42 as the needle is further extended into the container, without any rough or sharp edges of the needle cutting or biting into the seal 64.

While the hypodermic needle of the present invention has been described in conjunction with an automatic injector, it should be appreciated that this hypodermic needle has several other applications in the medical industry, such as syringes.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. An injection device comprising:

a container constructed and arranged to contain a medicament;

a medicament disposed within said container;

a seal constructed and arranged to seal the medicament in the container; and a hypodermic needle comprising a tubular, elongated, generally cylindrical wall defining an internal longitudinal bore extending longitudinally through the cylindrical wall along a longitudinal axis, said cylindrical wall forming a forward end defining a forward opening of said bore and a rearward end defining a rearward opening of said bore, said cylindrical wall having a laterally facing opening spaced closer to the rearward opening of said longitudinal bore than the forward opening of said longitudinal bore, said longitudinal bore being restricted at a position between said rearward opening and said laterally facing opening, said forward end having a point constructed and arranged to pierce an individual's flesh, said rearward end having a point constructed and arranged to pierce said seal so that said rearward opening and said laterally facing opening establish fluid communication with said medicament to enable said medicament to be dispensed through said bore and into the individual's flesh.

2. The injection device according to claim 1, wherein:

said rearward end of said needle terminates in an annular end surface having a rearwardmost point lying in an imaginary plane disposed perpendicularly to said longitudinal axis, said annular rearward end surface defining an imaginary plane inclined with respect to said imaginary plane perpendicular to said longitudinal axis, and wherein said laterally facing opening is generally in longitudinal alignment with said rearwardmost point so that when said rearward end pierces said seal, any tethered particle formed in said seal as a result will be disposed on a side of said hypodermic needle generally opposite a side on which said laterally facing opening is disposed.

* * * * *